(12) United States Patent
Rhee

(10) Patent No.: US 6,350,281 B1
(45) Date of Patent: Feb. 26, 2002

(54) METHODS AND APPARATUS FOR MEASURING VALVE ANNULUSES DURING HEART VALVE-REPLACEMENT SURGERY

(75) Inventor: Richard Rhee, Diamond Bar, CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

(21) Appl. No.: 09/396,124

(22) Filed: Sep. 14, 1999

(51) Int. Cl.$^7$ .................................................. A61F 2/06
(52) U.S. Cl. ......................................... 623/2.11; 33/512
(58) Field of Search ................................ 623/2.11, 2.4, 623/2.41, 912, 2.32; 33/512; 606/102

(56) References Cited

U.S. PATENT DOCUMENTS

| | | | |
|---|---|---|---|
| 4,211,241 A | 7/1980 | Kaster et al. ................ | 128/774 |
| 4,441,216 A | 4/1984 | Ionescu et al. .................. | 3/1.5 |
| 4,626,255 A | 12/1986 | Reichart et al. ................ | 623/2 |
| 5,042,161 A | 8/1991 | Hodge ...................... | 33/501.45 |
| 5,360,014 A | 11/1994 | Sauter et al. | |
| 5,471,756 A | 12/1995 | Bolanos et al. | |
| 5,489,296 A | 2/1996 | Love et al. ..................... | 623/2 |
| 5,531,785 A | 7/1996 | Love et al. ..................... | 623/2 |
| 5,584,878 A | 12/1996 | Love et al. | |
| 5,662,705 A | 9/1997 | Love et al. | |
| 5,814,098 A | 9/1998 | Hinnenkamp et al. | |
| 6,042,607 A | * 3/2000 | Williamson, IV et al. . | 623/2.11 |

FOREIGN PATENT DOCUMENTS

| | | |
|---|---|---|
| GB | 208362 A | 3/1982 |
| WO | WO94/18909 | 9/1994 |
| WO | WO95/16410 | 6/1995 |
| WO | WO96/40006 | 12/1996 |
| WO | WO97/25003 | 7/1997 |
| WO | WO97/41801 | 11/1997 |

OTHER PUBLICATIONS

Stephen Westaby, et al., Aortic Valve Replacement With the Freestyle Stentless Xenograft, The Society of Thoracic Surgeons 1995, pp S422–S427.

Stephen Westaby, et al., Time–Related Hemodynamic Changes After Aortic Replacement With the Freestyle Stentless Xenograft, The Society of Thoracic Surgeons 1995, pp 857–862.

Neal D. Kon, MD, et al., Comparison of Implantation Techniques Using Freestyle Stentles Porcine Aortic Valve, The Society of Thoracic Surgeons 1995, pp 857–862.

Medtronic, The Freestyle Aortic Root Bioprosthesis.

Dr. Richard J. Shemin Edwards Pericardial Bioprostheses—Sizing and Implantation, pp 50–62, Baxter Mini–Symposium, Chicago, IL, Apr. 24, 1993.

Baxter "Judge Our Pericardial Valve by its Appearance and You Will Only Get Half the Picture" pp 1–2.

A. Sidiropoulos, et al., Stentless Porcine Bioprostheses for all Types of Aortic Root pathology, European Journal of Cardio–Thoracic Surgery, 1997:11:917–921.

* cited by examiner

*Primary Examiner*—Bruce Snow
(74) *Attorney, Agent, or Firm*—Debra D. Condino; John Christopher James; Guy L. Cumberbatch

(57) ABSTRACT

A sizer measures a valve annulus to determine a size of an artificial heart valve to be sewn in the valve annulus during heart-valve replacement surgery. The sizer includes a support member and a resilient member. The support member has a size corresponding to the size of one of a plurality of artificial heart valves. The resilient member is disposed about the support member and has a resiliency substantially equal to the resiliency of a sewing ring of the artificial heart valve. Accordingly, when a surgeon inserts the sizer into a valve annulus, the resilient member conforms to the shape of the valve annulus much like the sewing ring will conform when positioned in the annulus and sewn in place. The surgeon is therefore able to determine more accurately the size of the annulus and, thereafter, to select a properly sized artificial valve.

26 Claims, 4 Drawing Sheets

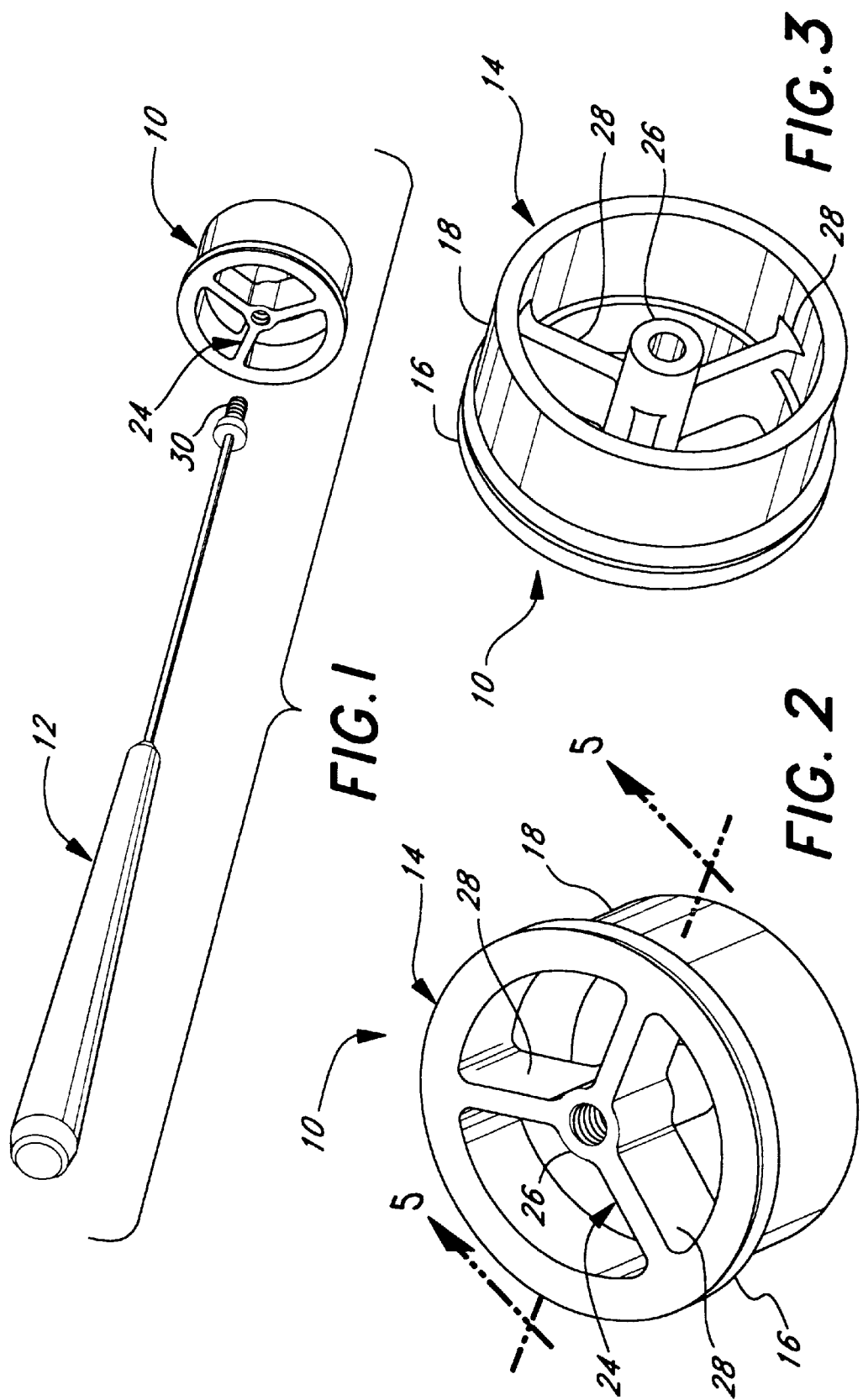

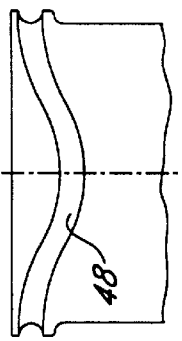
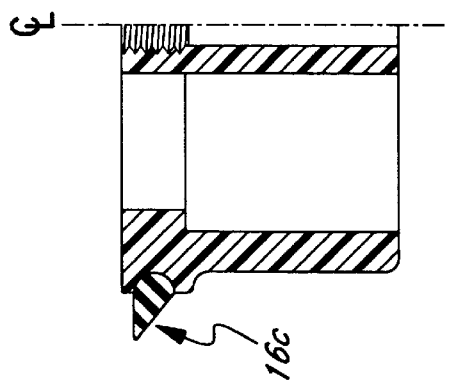
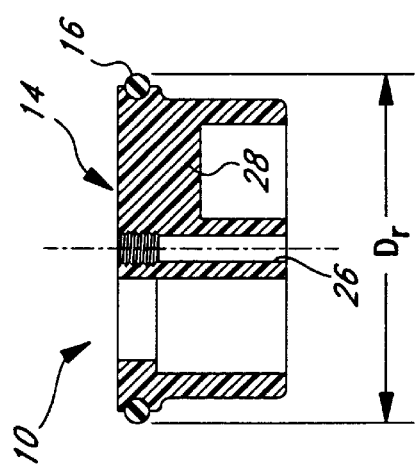
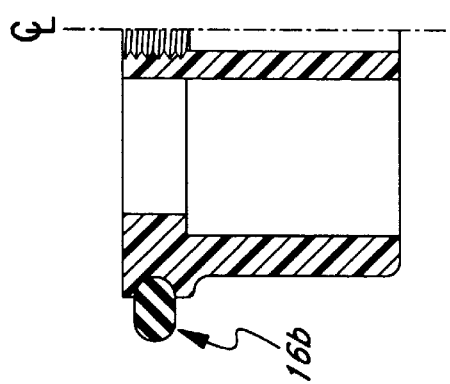
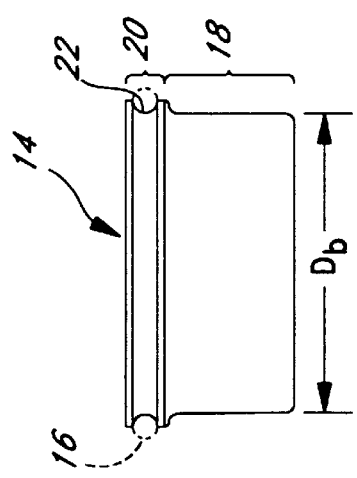
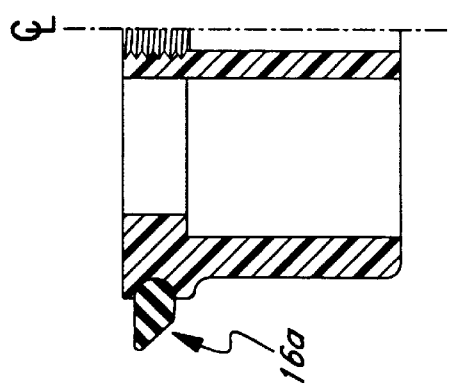

METHODS AND APPARATUS FOR MEASURING VALVE ANNULUSES DURING HEART VALVE-REPLACEMENT SURGERY

FIELD OF THE INVENTION

The present invention is directed to surgical apparatus and associated methods for measuring the size of a valve annulus (that is, the opening resulting from the removal of a diseased natural valve) during heart valve-replacement surgery. Valve annuluses need to be sized in order for a surgeon to select a properly sized replacement artificial valve.

BACKGROUND OF THE INVENTION

The heart has four valves—two on the right (the pulmonic and tricuspid) and two on the left (the aortic and mitraly)—that control the flow of blood through the chambers of the heart and out to the body. Although any of these valves may fail to function properly, disease most commonly affects the valves on the left side of the heart. The valves may narrow (called stenosis); the valves may not close all the way (causing a backflow of blood called regurgitation); or the valves may close incorrectly (called prolapse). A heart murmur represents the sound that a leaky or narrowed heart valve makes as blood moves through it.

The Aortic and Mitral Valves

Aortic stenosis is a narrowing of the aortic valve, through which blood flows from the left ventricle of the heart to the ascending aorta, the major artery whose branches supply blood to various parts of the body. Sometimes this narrowness is a congenital (i.e., inborn) defect, but more often the valve narrows as a consequence of aging, or of infections, such as rheumatic fever. Aortic stenosis results in the left ventricle having to work harder and harder to push blood out. As this occurs, the muscular walls of the ventricle thicken, increasing their requirement for oxygen. Symptoms of aortic stenosis include chest pain when the oxygen needs exceed the supply from the coronary arteries; fainting (syncope), if the valve becomes very tight; and congestive heart failure, which usually does not occur unless the valve has been narrowed for many years. Valve replacement, either with a mechanical or tissue valve often alleviates these symptoms.

In mitral stenosis, the valve opening between the upper and lower chambers on the left side of the heart has become narrowed. The cause is almost always rheumatic fever, which is now rare in most developed countries but is common in many parts of the world. When mitral stenosis occurs, the entry of blood into the left ventricle from the atrium is impeded by the narrow valve. Pressure builds up behind the valve, leading to an elevation of pressure in the lungs. This in turn may lead to shortness or breath (dyspnea), which is one of the major symptoms of mitral stenosis. Often, however, it occurs without any symptoms.

In aortic regurgitation, the aortic valve fails to close completely after the heart has pumped blood out into the aorta. Blood leaks back from the aorta into the left ventricle. In mitral regurgitation, improper closure causes blood to lead from the left ventricle back into the left atrium. In either case, the valve does not close properly because of a physical change in its shape or its support. This change may be the result of rheumatic fever; an infection (endocarditis), which may leave the valve scarred; or a heart attack, which causes loss of supporting muscle tissue. In the mitral valve, the change may be the result of a heart attack, which causes a loss of muscle tissue, or a spontaneous rupture of one of its muscular chords (chordea tendineae) that normally act as guide wires to keep it in place.

Major symptoms of defective mitral valves include fatigue, shortness of breath, and edema. Medications such as digitalis, diuretics, and angiotensin-converting enzyme (ACE) inhibitors can help alleviate symptoms. Some defective mitral valves can be reconstructed or, failing that, replaced by an artificial valve.

The Pulmonic and Tricuspid Valves

In the pulnonic and tricuspid valves, any narrowing is rare and almost always congenital. Leakage, or regurgitation, is unusual, but may occur when use of illicit intravenous drugs leads to infection that damages the valve. The infection, hallmarked by fever, often settles on these two valves because they are the first ones bacteria come in contact with as they travel through the bloodstream. If the valve becomes leaky, swelling of the abdomen and legs may occur. As with other valves, treatment can include replacement, but this is rare and usually not as effective as it is when the aortic or mitral valve is involved.

Artificial Valves

Valve-replacement surgery is usually recommended when the damage to the valve is severe enough to be potentially life-threatening, as in the case of severe aortic stenosis. The mitral and aortic valves are the heart valves that most often need to be replaced. Artificial valves have been in use since 1952, when Charles Hufnagel successfully replaced a patient's aortic valve with a caged-ball valve.

There are two types of artificial, or prosthetic, valves that can be used to replace the original valves: mechanical and tissue. Mechanical valves are made of synthetic materials, such as metal alloys, carbon, and various plastics. They come in two major designs: a "caged-ball valve" and a "tilting-disk valve." Tissue valves can be composed of animal or human valve tissue. Because of the scarcity of human valves available for transplantation, pig valves, specially processed and sutured into a synthetic cloth, are most often used. These valves are also called porcine valves. Pericardial valves make use of leaflets cut from the pericardium sac of a cow. Most tissue valves are well tolerated by the human body and are much less likely to require blood-thinning therapy, but they tend to be less durable: after 10 years, some 60 percent need to be replaced.

Both mechanical and tissue valves include some support structure or stent and a soft peripheral sewing ring. The sewing ring is used to secure the valve into place occluding the annulus, and must provide a good seal around the valve to prevent leakage.

Valve Replacement Surgery

Valve replacement is performed during open-heart surgery. The valves are mounted in an annulus comprising dense fibrous rings attached either directly or indirectly to the atrial and ventricular muscle fibers. In a valve replacement operation, the damaged leaflets are excised and the annulus sculpted to receive a replacement valve. Ideally the annulus presents relatively healthy tissue which can be formed by the surgeon into a uniform ledge projecting into the orifice left by the removed valve. The time and spatial constraints imposed by surgery, however, often dictate that the shape of the resulting annulus is less than perfect for attachment of a sewing ring. Moreover, the annulus may be calcified as well as the leaflets and complete annular debridement, or removal of the hardened tissue, results in a larger orifice and less defined annulus ledge to which to attach the sewing ring. In short, the contours of the resulting annulus vary widely after the natural valve has been excised.

The annulus is sized with an annulus sizer to determine the proper size of the replacement artificial valve. The artificial valve is then positioned in the opening and the sewing ring is carefully sutured or sewn to the tissue surrounding the valve opening. Given the uneven nature of the annuluses, the match between the valve sewing ring and annulus is a crucial aspect of prosthetic heart valve implantation. The annulus sizer is typically cylindrical, and made of hard plastic with a central threaded tap to which a handle is attached. A number of sizers are at a surgeon's disposal, each having a different size, or diameter. In use the surgeon inserts the sizer into the valve opening, measuring the size of the opening. An artificial valve properly sized for the valve opening is then selected and sewn in place.

Most annulus sizers are made from a biocompatible material and are rigid and inflexible. In contrast, the sewing rings of artificial valves are flexible. When inserted in the valve opening, the sewing ring may compress. The compression may result in the valve being too small for the valve opening. If this happens, the valve needs to be discarded, and a new valve needs to be chosen. As artificial valves are expensive to produce, discarding an artificial valve unnecessarily represents a tremendous waste. Also the time which is wasted in replacing improperly sized valves during the valve replacement surgery is critical to the patient and should avoided. Another possible error in sizing stems from using the rigid circular sizer to measure what is often an irregular annulus.

Accordingly, in view of the foregoing, it is an object of the present invention to provide annulus sizers which eliminate many of the drawbacks associated with conventional sizers.

SUMMARY OF THE INVENTION

It is thus an object of the present invention to provide annulus sizers which enable a surgeon to accurately select a properly sized artificial valve.

It is yet another object of the present invention to provide annulus sizers for measuring the size of valve openings which mimic the physical characteristics of an artificial valve sewing ring.

It is still another object of the present invention to provide methodology which enables surgeons to accurately determine the size of valve annuluses which, in turn, enables surgeons to select properly sized replacement artificial valves during valve replacement surgery.

These and other objects are achieved by the surgical apparatus and associated methods of the present invention which enable a surgeon to accurately measure the size of a valve annulus and then to properly selected a replacement artificial valve during valve-replacement surgery.

In accordance with a broad aspect of the invention, a sizer for measuring a valve annulus to determine a size of an artificial heart valve to be sewn in the valve annulus during heart-valve replacement surgery, includes a support member and a resilient member. The support member has a size corresponding to the size of one of a plurality of artificial heart valves. The resilient member is disposed about the support member and has a resiliency substantially equal to the resiliency of a sewing ring of the artificial heart valve. Accordingly, when a surgeon inserts the sizer into a valve annulus, the resilient member conforms to the shape of the valve annulus, analogous to how the sewing ring will conform when positioned in the annulus and sewn in place. The surgeon is therefore able to determine more accurately the size of the annulus and, thereafter, to select a properly sized artificial valve.

In addition to having substantially the same resilience as the sewing ring of an artificial heart valve, the resilient member also preferably is configured substantially the same as the sewing ring of the artificial heart valve. By substantially matching the artificial heart valve configuration, the sizer is able to "mimic" more accurately how the artificial heart valve will be received in the valve annulus for sewing.

The support member of the sizer is preferably releasably attachable to a surgical handle. Accordingly, in the operating theater, a surgeon is able to select a sizer and insert the sizer into the valve annulus to determine the size of the annulus. If the sizer does not fit to the surgeon's satisfaction, the surgeon is able to remove the sizer from the annulus, detach the sizer from the handle, select and attach another sizer of different size, and re-insert the new sizer into the annulus. This process may be repeated until the surgeon has determined the size of the valve annulus.

Other aspects, features, and advantages of the present invention will become apparent to those persons having ordinary skill in the art to which the present invention pertains from the following description taken in conjunction with the accompanying drawings.

BRIEF DESCRIPTION OF THE DRAWINGS

FIG. 1 is a perspective view of an exemplary sizer for measuring valve annuluses during heart valve-replacement surgery in accordance with the present invention, particularly illustrating the sizer in conjunction with a surgical handle;

FIG. 2 is a perspective view of the sizer of FIG. 1, particularly illustrating a proximal end thereof;

FIG. 3 is a perspective view of the sizer of FIG. 1, particularly illustrating a distal end thereof;

FIG. 4 is a side view of the sizer of FIG. 1;

FIG. 5 is a cross-sectional view of the sizer taken along line 5—5 of FIG. 2;

FIGS. 6A–C are cross-sectional views of sizers of the present invention with different cross-sectional shaped resilient members;

FIG. 8 is a side view of a sizer of the present invention having a scalloped groove for receiving a resilient member;

DETAILED DESCRIPTION OF THE INVENTION

Figures 7A, 7B:
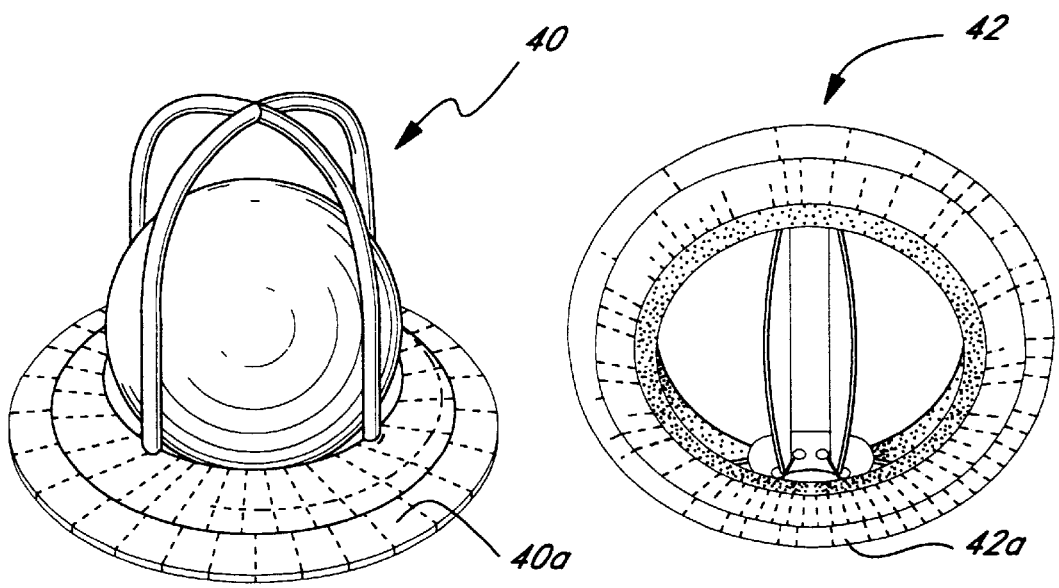
FIG. 7A is a perspective view of an artificial mechanical heart valve, particularly a caged-ball valve.
FIG. 7B is a perspective view of an artificial mechanical heart valve, particularly a tilting-disk valve.
Figures 7C, 7D:
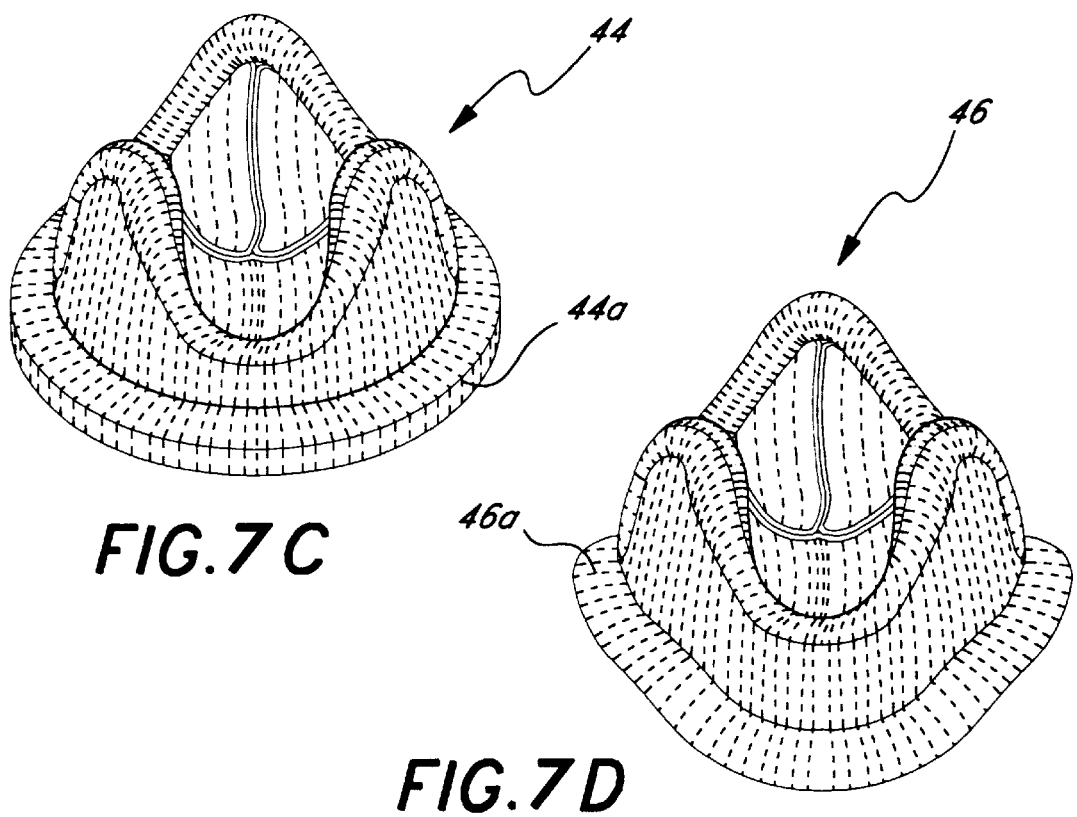
FIG. 7C is a perspective view of an artificial tissue heart valve for the mitral position.
FIG. 7D is a perspective view of an artificial tissue heart valve for the aortic position.

Referring to the drawings in more detail, an exemplary embodiment of a valve sizer 10 of the present invention is illustrated in FIG. 1 in conjunction with a surgical handle 12. With additional reference to FIGS. 2, 3, 4, and 5, exemplary sizer 10 includes a support member 14 and an annular or resilient member 16. Exemplary support member 14 has a body 18 and a retainer 20. The body 18 defines a distal portion of sizer 10, and the retainer 20 defines a proximal portion of the sizer.

The retainer 20 includes an annular or circumferential recess 22 for receiving and/or retaining resilient member 16, as particularly shown in FIGS. 4 and 5 (with the resilient member being shown in phantom line in FIG. 4). The resilient member 16 may be either removable from or integral with the retainer 20. The resilient member 16 has an outer diameter $D_r$ (FIG. 5) which is larger than an outer diameter $D_b$ (FIG. 4) of the body 18.

Exemplary support member 14 may be substantially tubular or cylindrical in configuration, with an attaching portion 24 disposed therein. As particularly shown in FIGS. 1, 2, and 3, the attaching portion 24 may include a threaded post 26 supported by a plurality of spokes 28. A threaded end 30 of the handle 12 may then be releasably attached to the threaded post 26 of the sizer 10.

Exemplary resilient annular member 16 may be substantially ring-like (toroidal) in configuration, for example, similar to an 0-ring. The annular recess 22 of the support member 14 is concave with a configuration complementary to the inner shape of the resilient member 16. Exemplary resilient member 16 is made from resilient material, such as a soft polymer, so as to be compressible and flexible.

Although a toroidal configuration of the resilient member 16 is illustrated, the resilient member 16 may be semi-rectangular, triangular, or elliptical, for example. With reference to FIGS. 6A–6C, various cross-sections of resilient member 16 are illustrated. FIG. 6A shows a semi-rectangular shaped resilient member 16a. To be precise, the member 16a includes an inner convex side 31, an outer angled side 32, a top side 33, and a bottom side 34 generally parallel with the top side. Because of the angled side 32 the top side 33 is longer than the bottom side 34. FIG. 6B illustrates an elliptical resilient member 16b with a minor axis parallel with the centerline CL of the valve and a major axis perpendicular thereto. Finally, FIG. 6C shows a resilient member 16c with a substantially triangular cross-section, except for a convex inner side.

As known in the art of artificial valves, sewing rings are made from a resilient material so as to conform to the valve annulus, that is, the opening resulting from the removal of the diseased natural valve. The resilient sewing ring may then be sutured to the tissue of the valve annulus. Exemplary resilient member 16 of the sizer 10 of the present invention has physical properties, particularly with respect to resilience and flexibility, substantially the same as those of sewing rings 46–50 common to artificial valves 40–44 in use today.

In addition, exemplary resilient member 16 is preferably configured substantially the same as the sewing rings; that is, if the sewing ring of a desired valve is elliptical in configuration, then the resilient member 16 may be substantially elliptical in configuration. In this regard, reference is made to FIGS. 7A–7D which respectively illustrate a caged-ball mechanical heart valve 40, a tilting-disk mechanical heart valve 42, a tissue valve 44 for the mitral annulus, and a tissue valve 46 for the aortic annulus. Each of the valves includes a sewing ring 40a, 42a, 44a, and 46a, respectively. The first three sewing rings 40a, 42a, and 44a are planar rings, while the sewing ring 46a for the aortic valve 46 may be scalloped, or undulating, around the periphery.

In order to conform to the shape of the corresponding sewing ring, it should be noted that the resilient members for the annulus sizers of the present invention may be planar rings or rings having a three-dimensional shape, so as to conform to the shape of a scalloped aortic valve sewing ring, for example. Indeed, such a sizer configuration is seen in FIG. 8 with the resilient member removed to exposed the scalloped channel 48. In this regard, the resilient member may be scalloped also, or may simply conform to the shape of the channel 48.

Figure 9A:
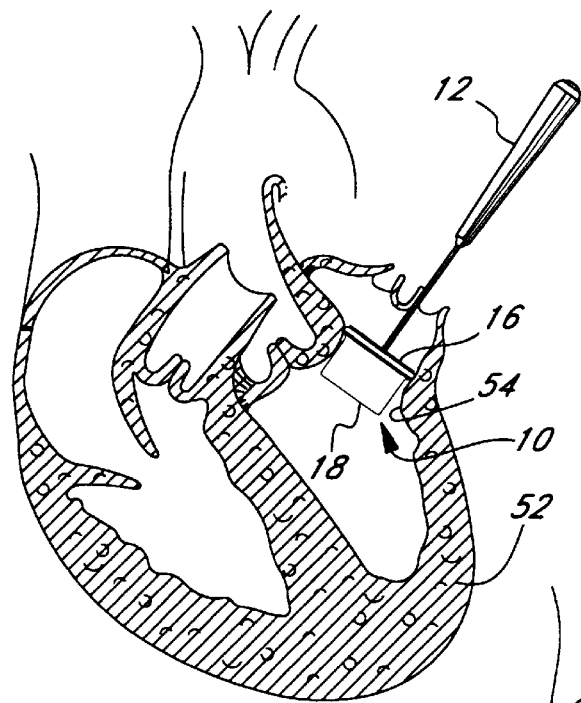
FIG. 9A is a schematic view of a heart illustrating a step in the methodology of the present invention in which a sizer is inserted into a valve annulus.
Figure 9B:
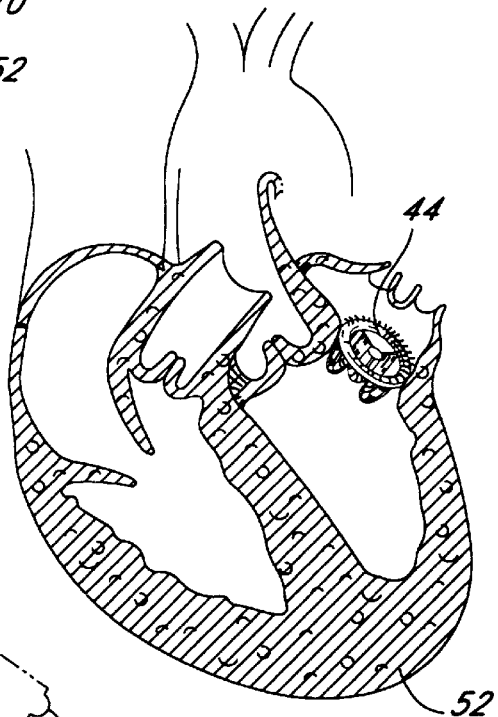
FIG. 9B is a schematic view of a heart illustrating another step in the methodology of the invention in which an artificial valve is sewn into a valve annulus.

Referencing FIGS. 9A and 9B, in use the sizer 10 may be attached to the handle 12 as described above. Access is made to the heart, which is referenced by numeral 52, particularly to a diseased heart valve, which is subsequently removed, as known in the art. Access may be according to conventional stemotomies or, more preferably, in accordance with minimally invasive procedures. When the valve is removed, a valve annulus 54 remains, the size of which is measured by exemplary sizer 10. A plurality of artificial valves may be provided, each with a sewing ring of unique size. A plurality of sizers 10 may also be provided. The body 18 and the resilient member 16 of each sizer are configured to corresponding to that of one of the artificial heart valves.

Figure 10:
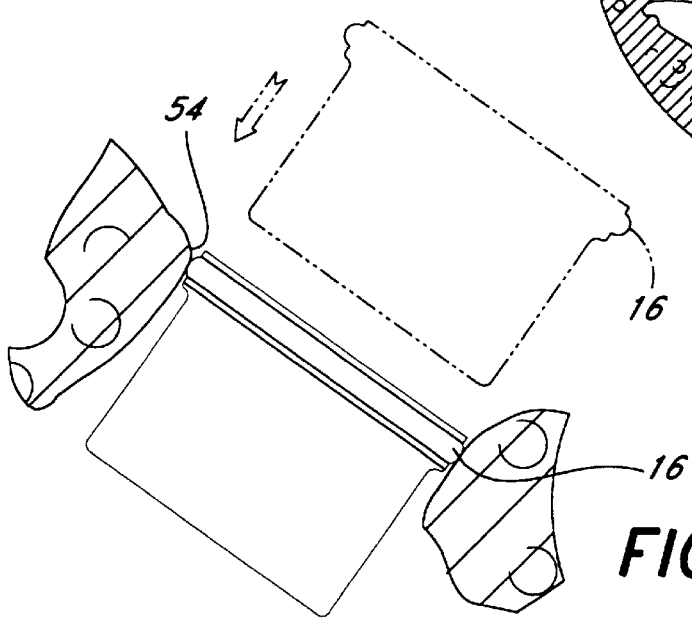
FIG. 10 is an enlarged schematic view of a sizer of the invention inserted into and urged against a valve annulus, particularly illustrating conforming features of a resilient member of the sizer.

To measure the size of the annulus 54, a surgeon selects a sizer 10 from the plurality of differently sized sizers. The outer diameters $D_b$ of the sizers may range, for example, from about 18 millimeters (mm) or 19 mm to about 35 mm or more. The distal body 18 of the sizer 10 is inserted into through the valve annulus 54 until the resilient member 16 abuts the valve annulus 54. The resilient member 16 conforms to the shape of the valve annulus 54. The valve annulus 54 may be irregular in shape, with portions thereof more hard than other portions due to calcification. Accordingly, the resilient member 16 is able to compress in response to relatively hard portions of the annulus 54, thereby conforming to the shape of the annulus. More specifically, as particularly shown in FIG. 10, the resilient member 16 is able to compress from a normal position, shown in phantom line, to a compressed positioned when urged against the annulus 54, as shown by solid line, thereby conforming to the shape of the annulus. This conforming feature of the invention allows a surgeon to determine accurately the size of the annulus and select a properly sized replacement valve.

If the resilient member 16 does not conform to the valve annulus 54 in a desired manner, the surgeon may remove the sizer 10 and replace it with a differently sized diameter, which may then be inserted into the valve annulus 54. This process may be repeated until the surgeon has determined the size of the annulus 54 to his or her satisfaction. The surgeon may then select a properly sized valve (e.g., valve 44), position the valve 44 in the annulus 54, and suture the sewing ring 50 to the annulus, as shown in FIG. 9B.

With further reference to FIGS. 2–5, the exemplary embodiment of the sizer 10 of the invention illustrated in the drawings is a two-piece configuration: the support member 14 and the resilient member 16. The support member 14 may be made from substantially rigid material (i.e., having little resilience when compared to the resilient member 16) to withstand forces required to insert the sizer 10 into a valve annulus. Alternatively, the sizer 10 may be a one-piece design, with the resilient member 16 permanently attached or integral with the support member 14. In the one piece embodiment, the support member 14 may be made from material which is either rigid or resilient. In a resilient embodiment of the support member 14, the body 18 is able to conform to a relatively hard and/or calcified annulus. In any case, the resilient member 16 is made from material which is substantially analogous to that of sewing rings of artificial valves commonly used today.

In addition to the substantially cylindrical configuration of the sizer 10, the support member 14 may be configured in other shapes; for example, the support member 14 may be elliptical, oval, kidney-shaped, and so on.

The handle 12 is preferably bendable to provide the surgeon with an implement that may reach difficult-to-access areas of the heart 52. In this regard, the handle 12 may be configured in accordance with a handle disclosed in U.S. Pat. No. 6,004,329, issued Dec. 21, 1999, filed Feb. 27, 1998, the entire disclosure of which is incorporated herein by reference.

The resilient member 16 of the present sizer may be formed integrally with the support member 14, or may be removable. In the letter case, the resilient member 16 may be provided as a disposable item, while the support member 14 is reusable. The support member 14 is desirably made of a rigid material, such as polypropylene or polycarbonate, that is capable of being sterilized in an autoclave. The resilient member 16 can be used once, and then thrown away. A set of resilient members 16 for any one support member 14 may be provided, or replacement resilient members can be obtained separately. In addition, for any one support member 14, a number of different shaped resilient members 16 may be supplied. So, for example, a fall set of sizers may include a plurality of different sized support members 14, with toroidal, elliptical, triangular, and irregularly-shaped resilient members 16 for each support member size.

Those skilled in the art will understand that the embodiments of the present invention described above exemplify the principles of the invention and do not limit the scope of the invention to those embodiments of the surgical apparatus specifically illustrated in the drawings and described above. The exemplary embodiments provide a foundation from which numerous alternatives and modifications may be made, which alternatives and modifications are also within the scope of the present invention as defined in the appended claims.

What is claimed is:

1. A sizer for measuring a valve annulus to determine a size of an artificial heart valve to be sewn in the valve annulus during heart-valve replacement surgery, the artificial heart valve including a sewing ring having a resiliency, said sizer comprising:
    a support member having an annulus measuring body with a length sufficient for insertion into a heart valve annulus and a retainer provided on a periphery of the support member adjacent to the annulus measuring body; and
    a resilient member removable from and held within the retainer of said support member so as to project outward to a size greater than that of the annulus measuring body;
    said resilient member having a resiliency substantially the same as the resiliency of the sewing ring of the artificial heart valve.

2. A sizer as claimed in claim 1 wherein said annulus measuring body is cylindrical and has an outer diameter.

3. A sizer as claimed in claim 1 wherein said retainer comprises a concave peripheral recess for retaining said resilient member.

4. A sizer as claimed in claim 1 wherein said support member includes an attaching portion for attaching to a handle.

5. A sizer as claimed in claim 1 wherein said resilient member is configured substantially the same as the sewing ring of the artificial heart valve.

6. A sizer as claimed in claim 5 wherein said resilient member is substantially toroidal in configuration.

7. A sizer as claimed in claim 5 wherein said resilient member is three-dimensional in configuration.

8. A sizer as claimed in claim 7 wherein said resilient member is scalloped.

9. A sizer as claimed in claim 5 wherein said resilient member has an elliptical cross-section.

10. A sizer as claimed in claim 5 wherein said resilient member has a substantially triangular cross-section with a convex inner side.

11. A sizer for measuring a valve annulus, said sizer comprising:
    a support member having a length and a distal portion and a proximal portion spaced along the length, and a periphery sized for insertion distal portion first into a heart valve annulus; and
    a resilient member disposed about and extending outward from the periphery of the proximal portion of said support member;
    said resilient member being adapted to conform to the shape of the valve annulus when urged thereagainst.

12. A sizer as claimed in claim 11 wherein said support member is attachable to a surgical handle.

13. A sizer as claimed in claim 11 wherein said support member is substantially rigid.

14. A sizer as claimed in claim 11 wherein said support member is resilient.

15. A sizer as claimed in claim 11 wherein said resilient member is integral with said support member.

16. A sizer as claimed in claim 11 wherein said resilient member is removable from said support member.

17. A sizer as claimed in claim 16 wherein said support member includes a peripheral groove sized to receive the resilient member.

18. A sizer as claimed in claim 17 wherein said peripheral groove is three-dimensional in configuration.

19. A sizer as claimed in claim 17 wherein said peripheral groove is scalloped.

20. A sizer as claimed in claim 11 wherein said support member has a cylindrical distal body and a peripheral retainer disposed about a proximal end thereof, wherein said resilient member is held by and removable from the peripheral retainer.

21. A method for measuring a size of a valve annulus to determine a proper size of an artificial valve when replacing a natural heart valve of a heart, said method comprising the steps of:
    providing a plurality of artificial heart valves, each of said artificial heart valves having a resilient sewing ring of unique size;
    providing a plurality of sizers, each of said sizers including a support member and a resilient member disposed about a periphery of said support member, each said resilient member of said sizers having a size corresponding to that of one of said artificial heart valves;
    selecting one of said sizers to define a selected sizer;
    attaching a handle to said support member of said selected sizer;
    inserting said selected sizer into the valve opening;
    determining whether said selected sizer approximates the size of the valve annulus; and
    selecting an artificial heart valve which has a sewing ring with a size corresponding to that of said attached sizer.

22. A method as claimed in claim 21 wherein the step of providing a plurality of sizers includes providing more than one resilient member for each sizer.

23. A method as claimed in claim 21 wherein the resilient members provided for each sizer have different cross-sectional shapes.

24. A surgical apparatus for measuring a valve opening to determine a proper size of an artificial heart valve during heart-valve replacement surgery, the artificial heart valve including a sewing ring having a resiliency and a configuration, said surgical apparatus comprising:

a handle; and a sizer having at most two separate elements including a support member connectable to said handle and having a cylindrical portion long enough for insertion into a heart valve annulus and a resilient member disposed about a periphery of said support member adjacent the cylindrical portion;

said resilient member having resiliency substantially equivalent to the resiliency of the sewing ring of the artificial heart valve.

25. Surgical apparatus as claimed in claim 24 wherein said resilient member has a cross-sectional shape substantially the same as the configuration of the sewing ring.

26. Surgical apparatus as claimed in claim 24 further comprising a plurality of said sizers, said plurality of said sizers including sizers of different size.

* * * * *